United States Patent [19]
Stouffer et al.

[11] Patent Number: 5,617,864
[45] Date of Patent: Apr. 8, 1997

[54] METHOD AND APPARATUS FOR POSITIONING AN ULTRASONIC TRANSDUCER AND A DISPLAY SCREEN

[75] Inventors: James R. Stouffer; Yujun Liu, both of Ithaca; Steven K. Newman, Lansing, all of N.Y.

[73] Assignee: Animal Ultrasound Services, Inc., Ithaca, N.Y.

[21] Appl. No.: 511,563

[22] Filed: Aug. 4, 1995

[51] Int. Cl.⁶ ........................................................ A61B 8/00
[52] U.S. Cl. ......................................................... 128/662.03
[58] Field of Search ........................ 128/660.04, 660.05, 128/660.09, 660.1, 662.03

[56] References Cited

U.S. PATENT DOCUMENTS

| | | |
|---|---|---|
| 3,496,764 | 2/1970 | Stouffer . |
| 3,603,303 | 9/1971 | Stouffer . |
| 3,688,564 | 9/1972 | McDicken . |
| 3,709,029 | 1/1973 | Hurwitz . |
| 3,722,263 | 3/1973 | Hautaniemi et al. . |
| 3,742,756 | 7/1973 | Seager . |
| 3,854,471 | 12/1974 | Wild . |
| 3,964,296 | 6/1976 | Matzuk . |
| 3,964,297 | 6/1976 | Jorgensen et al. . |
| 4,094,306 | 6/1978 | Kossoff . |
| 4,099,420 | 7/1978 | Stouffer et al. . |
| 4,130,112 | 12/1978 | Frazer . |
| 4,186,747 | 2/1980 | Iinuma . |
| 4,359,055 | 11/1982 | Carlson . |
| 4,359,056 | 11/1982 | Carlson . |
| 4,545,385 | 10/1985 | Pirschel . |
| 4,603,701 | 8/1986 | Chen . |
| 4,625,731 | 12/1986 | Quedens et al. . |
| 4,664,124 | 5/1987 | Indle et al. . |
| 4,772,346 | 2/1982 | Chen . |
| 4,785,817 | 11/1988 | Stouffer . |
| 4,844,080 | 7/1989 | Frass et al. ............... 128/662.03 |
| 4,870,970 | 10/1989 | Gray et al. . |
| 4,931,933 | 6/1990 | Chen et al. . |
| 5,014,713 | 5/1991 | Roper et al. . |
| 5,028,440 | 7/1991 | Nissen . |
| 5,078,147 | 1/1992 | Reid . |
| 5,079,951 | 1/1992 | Raymond et al. . |
| 5,140,988 | 8/1992 | Stouffer et al. . |

FOREIGN PATENT DOCUMENTS 0337661  6/1989  European Pat. Off. .

OTHER PUBLICATIONS

Gillis, W., Jan. 1971, An Evaluation of Indicues of Carcass Yield, Physical Composition and Chemical Composition in Swine; and Ultrasonic Measurement of the Longisimus Doris Area and Fat Thickness in Beef and Swine.

Wongkhalaung, T., Jun. 1975, Pregnancy Detection and Changes During Gestation in Swine Determined with Ultrasound.

The CSB Ultra–Meater, CSB System, Grading Hog Carcasses.

Gresham et al, J. Anima. Sci., 1992, Commercial Adaption of Ultrasonography to Predict Pork Carcass Compositions of Live Animal and Carcass Measurements, pp. 631–639.

(List continued on next page.)

Primary Examiner—George Manuel
Attorney, Agent, or Firm—Barnard, Brown & Michaels, P.C.

[57] ABSTRACT

Disclosed herein is a system for positioning an ultrasonic transducer where the user can see the positioning device and a display of the image being generated at the same time. This system solves the problem of the user having to look away from the transducer to see the image. The method comprises positioning a display screen to show the ultrasonic image being generated to the user such that the user can see the positioning of the transducer and the image on the display screen at the same time. To accomplish this the display screen can be incorporated into or mounted directly mounted onto the transducer housing. Once the user properly positions the transducer and is satisfied with the image, a image capture signal can be sent by the user. Once the image is captured it can be sent to an associated computer for analysis, printed or saved for archiving, etc.

16 Claims, 4 Drawing Sheets

OTHER PUBLICATIONS

Stouffer, J., Using Ultrasound Objectively Evaluate Composition and Quality of Livestock, 21st Century Concepts, pp. 49–53.

Scamogram, model 722, Ithacao, Inc., Ultrasonic Animal Scanner.

Stouffer, J., Ultrasonics for Live Lamb an Carcass Evaluation, 1988 Proceeding Sheep Industry development Program, Denver, Colorado.

Syllabus –Animal Ultrasound Seminar & Wet–Lab, Oct. 13–15, 1989.

Ultrasonographic Evaluation of the Urinary System and Prostate Gland in the Dog and Cat –R. Badertscher –Veterinary Imaging Professional.

Meat and Poultry Inspection –National Academy Press –1985.

Tendon and Ligament Ultrasound in the Equine Athlete –A. Kent Allen, Allen–Schneigder Equine Hospital.

A Review of Potential New Methods of On–line Pork Carcass Evaluation –Forrest et al –J. Anim. Sci 1989 –67:2164–2170.

A Review of Ultrasonic Application in Animal Science –J.R. Stouffer –Journal of Clinical Ultrasound –vol. 5, Apr. 1977.

Ultrasound for Animal Evaluation –J.R. Stouffer –New York's Food and Life Sciences –vol. 10., No. 3, 1977.

Ofjective Technical Methods for Determining Carcass Value in Live Animals With Special Emphasis on Ultrasonics–J.R. Stouffer –World Review of Animal Production, 1966.

Mild Exercise –Effect on Body Composition and Metabolism, Stouffer et at –N.Y. State Journal of Med. –Aug. 1974.

Relationship of Ultrasonic Measurements and X–Rays to Body Composition –J.R. Stouffer –Animals of the N.Y. Academy of Sci, vol. 110, Prt 1. pp. 31–39 –Sep. 1963.

Ultrasonics for Evaluation of Live Animal and Carcass Composition –J.R. Stouffer –Twelfth Research Conference –pp. 81–87.

Development and Application of Ultrasonic Methods for Measuring Fat Thickness and Rib–Eye Area in Cattle and Hogs –J.R. Stouffer et al, Journal of Animal Sci., vol. 20, No.4. Nov. 1961.

Ultrasonic News –Winter 1960 –vol. IV No. 4.

Comparison of Methods Used for Carcass Evaluation in Swine, Doornenbal et al –Jou. of Ani. Sci., vol. 21, No. 3, Aug., 1962.

Techniques for the Estimation of the Composition of Meat Animals –J.R. Stouffer, pp. 207–219.

Status of the Application of Ultrasonics in Meat Animal Evaluation –J.R. Stouffer –pp. 161–173.

Ultrasonic Research in Europe –J.R.Stouffer –Mar.–Aug. 1962.

The Ultrasonic Approach to Measuring Fat and Muscling in Live Beef Cattle –J.R. Stouffer –pp. 34–35.

Carcass Evaluation and Its Research Applications –J.R. Stouffer –1961 –pp. 32–36.

Application of Ultrasound in the Livestock and Meat Industry, J.R. Stouffer –pp. 310–315.

Meat Evaluation in Live Animals –J.R. Stouffer –Frontiers in Food Research, Cornell University, Apr. 12–13, 1966, pp. 102–108.

Muscle Metabolism and Real–Time Ultrasound Measurement of Muscle and Subcutaneous Adipose Tissue Growth in Lambs Fed Diets Containing a Beta–Agontst, Stouffer et al, J. Anim. Sci. 1986, 63:1410–1417.

Estimating Fattiess in Horses and Ponie, Stouffer et al, Jour. Anim. Sci., vol. 43. No. 4 (1976).

Syllabus –2nd Annual AIUM Animal Ultrasound Seminar & Wet–Lab, American Institute of Ultrasound in Medicine –1990.

The Use of Ultrasound to Predict the Carcass Comosition of Live Cattie –A Review –Animals Breeding Abstracts –G. Simm, vol:51 No. 12, 1983.

Ultrasonic Determination of Body Composition –Dec. 1968, J.R. Stouffer.

Studies on the Pathogenesis of Staphylococcal Osteomyelitis in Chickens, –I. Effect of Stress on Experimentally Induced Osteomyelitis; Mutalib et al –Avian Dis., vol. 27, No.1. Jan.–Mar. 1983, 141–156.

Ultrasonics of Postmortem Detection of Animal Diseases and Abnormalities –J.R. Stouffer –Seminar for FSIS–USDA –Sep. 18, 1985.

Die Anwendung Non Ultraschallmessungen In Den USA, J.R. Stouffer, pp. 64–70.

Real Time Ultrasound Evaluation –J.R. Stoffer –Jun. 1988.

Relationships of Empty–Body Composton and Fat Distribution to Live Anmal and Carcass Measurements in BOS Indicus –BOS Taurus Crossred Cows –Holloway et al, pp. 1818–1826.

METHOD AND APPARATUS FOR POSITIONING AN ULTRASONIC TRANSDUCER AND A DISPLAY SCREEN

FIELD OF THE INVENTION

The invention pertains to ultrasonic transducer positioning devices in the field of ultrasonic evaluation of animals and carcasses with ultrasound. More particularly, the invention pertains to an ultrasonic transducer positioning device wherein the display screen and the ultrasonic transducer are within the same unit so the user can view the ultrasonic image and the positioning of the transducer at the same time.

BACKGROUND OF THE INVENTION

Evaluating and grading meat animals, both live and slaughtered, have been historically performed by humans. Because of this it is very difficult to achieve accuracy, efficiency and consistency. Both producers and packers demand an objective means of classifying their animals accurately according to their carcass real values. However, since an accurate, quick, and consistent grading system has not been put into place, producers are not being paid for the true value of their animals. Currently, producers are paid on an average basis. The price differential between a high-yield and a low-yield grade is less than it should be. Therefore, it is important to the meat industries that improved or new technologies must be developed in their evaluation systems in order to be able to accurately measure the animal or carcass characteristics that are of significant value.

Typically, ultrasonic images of the Longissimus dorsi (rib eye muscle in beef and loin eye muscle in hogs) have been used to evaluate livestock. This has been done by positioning a linear transducer (scan line is in the same direction as the linear transducer) in either a perpendicular or parallel direction with respect to the backbone of the livestock. Previously, many types of positioning apparatus have been implemented for consistently positioning a transducer in a transverse (perpendicular) position along the backbone of an animal or carcass. For example, see U.S. Pat. Nos. 4,785,817; 4,099,420; 3,603,303; and 3,496,764 each granted to James R. Stouffer, one of the coinventors of the present invention. As shown in the sales catalog for ITHACO's SCANOGRAM, a guide-cam set Type C was available for linear scans consisting of a series of individual scans in a linear direction.

EPO Patent application publication number 0 337 661 A1, entitled, "Method and apparatus for grading of live animals and animal carcasses" teaches method and apparatus for longitudinal (parallel to the backbone) scanning and image recognition to determine automatically fat and muscle characteristics. Wilson was not the first to use longitudinal scanning to evaluate carcasses, as shown by the Phd thesis by Wayne A. Gillis entitled "An Evaluation of Indices of Carcass Yield; Physical Composition and Chemical Composition in Swine; and Ultrasonic Measurement of the Longissimus Dorsi Area and Fat Thickness in Beef and Swine", which shows longitudinal scanning. Another group currently using longitudinal scanning is CSB-SYSTEM of America Corporation.

Neither Wilson, Gillis or CSB teach some of the problems associated with performing longitudinal scans or method or apparatus for consistently locating the transducer on the animal or carcass. One problem with longitudinal scanning occurs when the transducer is parallel to the back fat layers. Artifacts or multiples of the fat layers and the muscle/fat interface show up in the image of the muscle layer. These multiples occur as a result of the sound waves rebounding directly back off of these layers and interfere with image recognition apparatus methods for determining muscle and fat composition. As can be seen by the advertising literature, the CSB system has the problem of artifacts as shown in the ultrasound image displayed on the first page.

These problems were solved by the methods and apparatus for positioning an ultrasonic transducer for longitudinal scanning of an animal or carcass taught in U.S. Pat. No. 5,316,003 granted on May 31, 1994. This system comprises positioning the transducer such that it is not parallel to the rib line, thus eliminating artifacts. Although, this system greatly improved scan quality and reliability for commercial use, further improvements needed to be made.

Like all the other systems known to be in use at this time, the positioning device shown in U.S. Pat. No. 5,316,003 requires the user to first position the transducer on the animal or carcass and then look away from the transducer to check the image on a display screen separate from the transducer (See FIG. 1 of U.S. Pat. No. 5,316,003). Even this slight turning by the user was sometimes enough to jar the transducer. An experienced user would quickly realize that proper positioning or contact had been lost when looking at the display. However, the line speeds in a packing plant require an operator to evaluate one carcass every three seconds. Therefore, there is little time to reposition a transducer. Furthermore, a system for use in a commercial setting must be capable of producing reliable data regardless of the experience level of the operator.

The present invention includes the discovery of the problems described herein and their solutions.

SUMMARY OF THE INVENTION

It is a primary objective of this invention to provide apparatus and method for positioning an ultrasonic transducer on an animal or carcass to be evaluated where the user can see the positioning device and a display of the image being generated at the same time. This system solves the problem of the user having to look away from the transducer to see the image.

The method of positioning an ultrasonic transducer and display screen on an animal or carcass to be evaluated by ultrasonic detection equipment, is novel. The method comprises positioning a display screen to show the ultrasonic image being generated to the user such that the user can see the positioning of the transducer and the image on the display screen at the same time. To accomplish this the display screen can be incorporated into or mounted directly mounted onto the transducer housing.

Once the user properly positions the transducer and is satisfied with the image, an image capture signal can be sent by the user. Once the image is captured it can be sent to an associated computer for analysis, printed or saved for archiving, etc. The image capture signal can be provided by a switch or button and can be activated by the user. The switch can either be located directly on the transducer housing or be provided by some other means accessible by the user if there is a concern that the activation of the switch could disrupt the position of the transducer.

The transducer and display positioning apparatus of the present invention can also include any of the features of the transducer positioning device taught in U.S. Pat. No. 5,316,003 such as the tail bone pin for locating the transducer with respect to a tail region of the animal or carcass, the back position pin for locating the transducer with respect to a backbone of the animal or carcass, or a counterbalance support to avoid user fatigue.

While, the transducer and display positioning apparatus of the present invention was developed primarily for use with animals or carcasses, it can also be used with humans. Ultrasound equipment is used routinely by the medical profession as a diagnostic tool. Ultrasound equipment operators may not have the same time pressures as found in a commercial packing, plant but still have the problem of having to look away from the transducer and their patients to see the image on a display screen. This can be tiresome to the operator and annoying to the patient. By using the present invention the operator would be able to obtain high quality images and look at the patient the entire time.

A more complete understanding of the invention and its advantages will be apparent as the detailed description is considered in connection with the accompanying drawings.

DESCRIPTION OF THE PREFERRED EMBODIMENT

Figure 1:
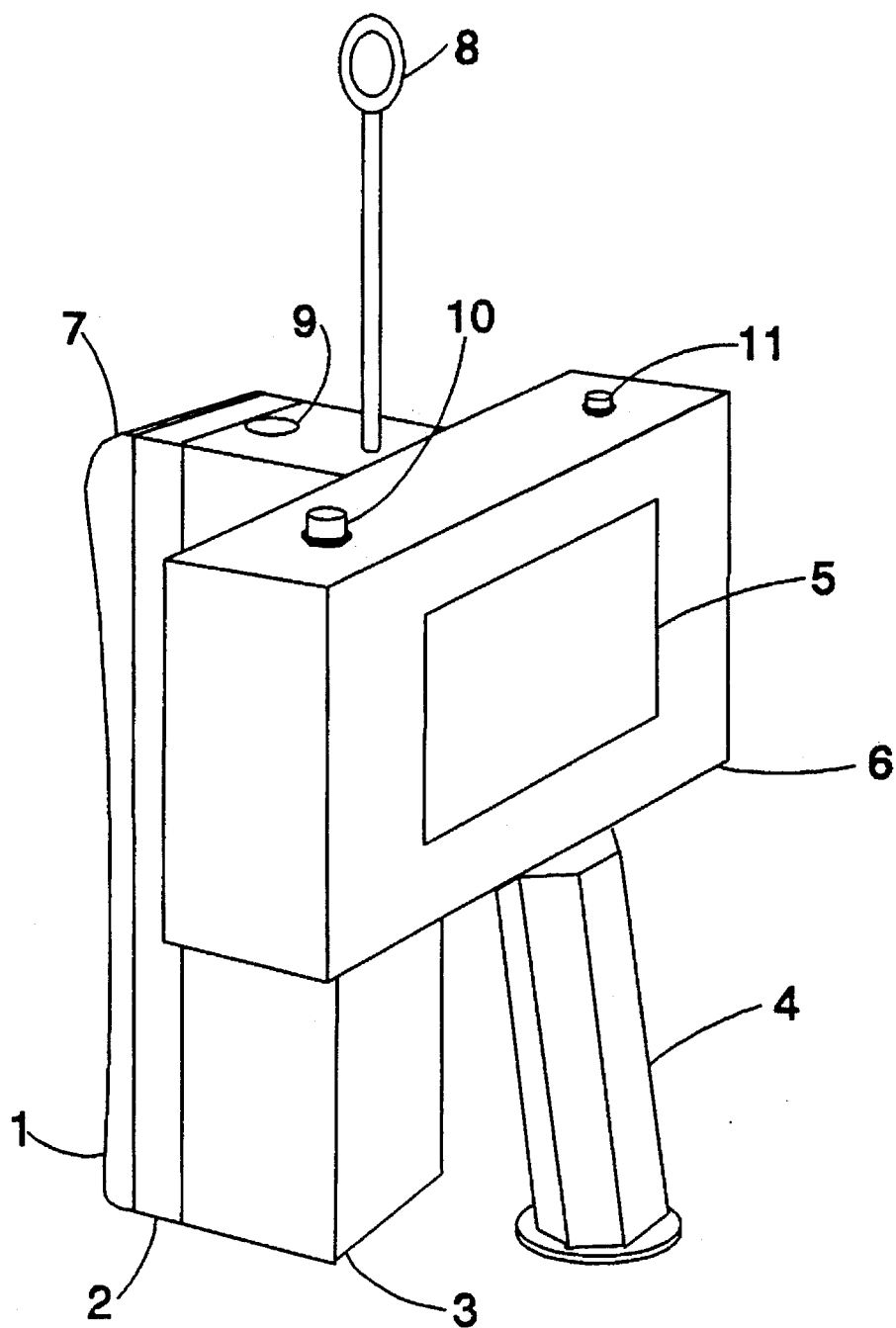
FIG. 1 shows an orthogonal view of the embodiment of the invention.

For the purposes of promoting an understanding of the teachings of the present invention, references will now be made to the embodiments illustrated in the drawings and specific language will be used to describe these embodiments. It will nevertheless be understood that no limitation to the scope of the invention is thereby intended, alterations and further applications of the teachings of the present invention as illustrated and described hereinabove is anticipated by those skilled in this art.

FIG. 1 is an orthogonal view of an embodiment of the positioning apparatus taught by the present invention. The transducer positioning apparatus is designed to position an ultrasonic transducer 1 on an animal or carcass to be evaluated by ultrasonic detection equipment. The ultrasonic transducer 1 is contained within a two part transducer housing 2 and 3. The transducer housing is comprised of a transducer housing face 2 and a transducer housing body 3. The apparatus includes a pistol grip type handle 4 to ensure steady and constant positioning on the animal or carcass.

The user view screen 5 is shown contained within a general viewer housing 6 which is attached to the pistol grip type handle 4. The purpose of combining the view screen 5 and the positioning apparatus within one unit is to avoid the time consuming and inaccurate process of continually looking back and forth between the ultrasonic positioning apparatus and the animal or carcass.

This process of continually looking back and forth between the ultrasonic positioning apparatus and the carcass can lead to significant problems in the manufacturing situation. At a normal line speed of one carcass per every three seconds it is quite difficult for an individual to get the ultrasonic positioning apparatus into place, then turn to look at the viewer screen and finally to look back at the apparatus to depress the trigger. This invention has solved that problem by combining all of the essential elements in one complete handheld unit.

Proper evaluation of the animal or carcass requires that the ultrasonic transducer 1 be steady and that unbroken contact be maintained between the standoff guide 7 and the animal or carcass. These two requirements are attained using the present invention with its user view screen 5 and positioning apparatus combined in one handheld unit.

An counter balance hook 8 is included to allow a user to attach the positioning apparatus to a counter balance. Counter balances are commonly used in manufacturing situations. Use of a counter balance will alleviate the user fatigue associated with handling of the transducer positioning apparatus. A sealed, watertight cable 9 transmits information to the computer that is to be returned to the user view screen to allow grading of the animal or carcass.

Figure 2:
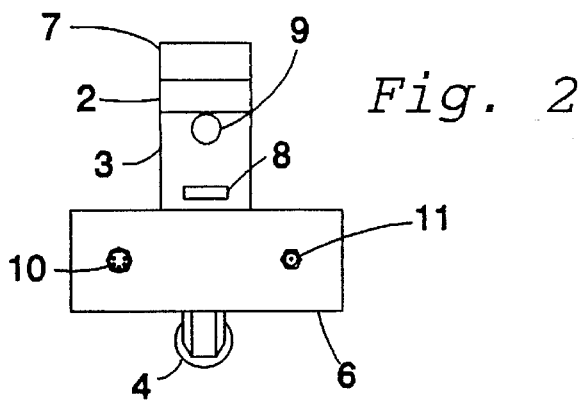
FIG. 2 shows a view of the embodiment of the invention with a six pin connector and coaxial connector visible.

FIG. 2 shows a top view of the embodiment of the invention with a six pin connector 10 and a coaxial cable connector 11 visible. The six pin connector 10 and the coaxial cable connector 11 are connected to the top of the general viewer housing 6. The six pin connector 10 provides two pins for power to the user view screen 5, two pins for the trigger switch 12, and two pins that are free. The coaxial cable connector 11 provides the means of transmitting the on-screen image between the computer and the user view screen 5. The computer and ultrasonic equipment currently being used in this process include: 1) an Aloka 500 V console, 2) an Aloka 5049 V-3.5 transducer, 3) a scanning head with a Citizen 2.9 inch monitor, and 4) a 486 computer.

Figure 3:
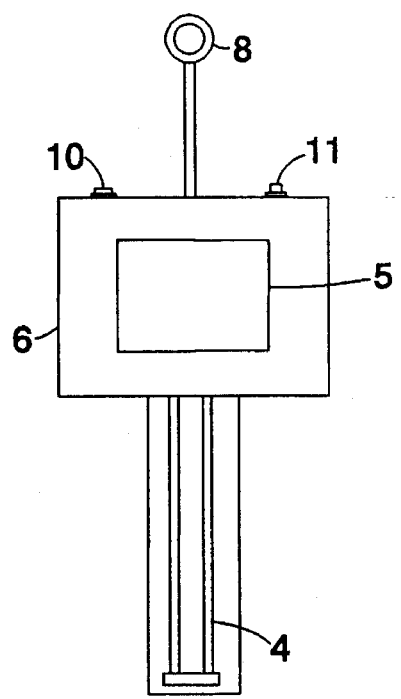
FIG. 3 shows a front view of the embodiment of the invention with the viewer screen and counter balance visible.

FIG. 3 shows a front view of the embodiment of the invention with the user view screen 5 and general viewer housing visible 6. The positioning of the user view screen 5 on the pistol grip type handle 4 of the transducer positioning apparatus is essential to the invention. This combination allows the user to view the image on the view screen 5 while positioning the ultrasonic transducer apparatus on the animal or carcass, thus eliminating the inaccuracies associated with using two separate mechanisms. This essential element of the invention has solved many of the problems that have arisen with positioning the ultrasonic transducer apparatus and acquiring a quality image of the animal or carcass.

The user view screen 5 is a standard video display monitor that is small enough to fit into the encompassing general viewer housing 6. Connections for the video display monitor are standard video display components. The general viewer housing 6 is a sealed, water tight casing made of plastic or stainless steel.

Figure 4:
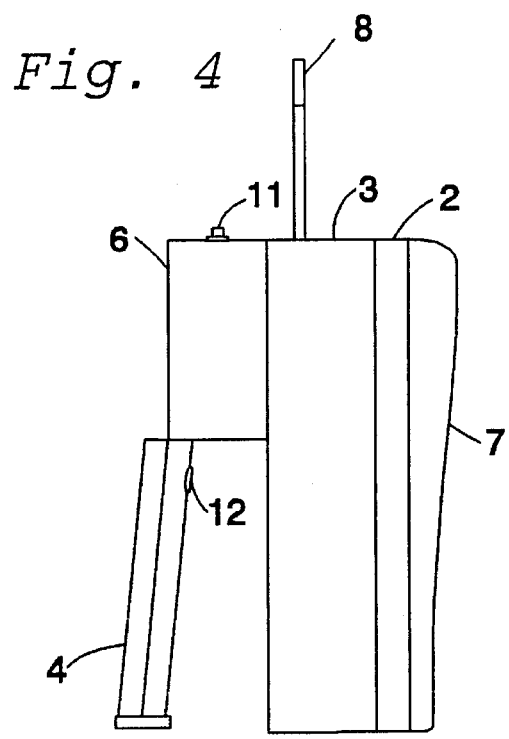
FIG. 4 shows a side view of the embodiment of the invention with the pistol grip type handles and standoff guide visible.

FIG. 4 shows a side view of the embodiment of the invention with the pistol grip type handle 4, trigger switch 12, and standoff guide 7 visible. The trigger switch 12, located on the pistol grip type handle 4, allows the user to record the ultrasonic image of the animal or carcass when the ultrasonic positioning apparatus is in proper position. The positioning of the trigger switch 12 on the pistol grip type handle 4 is the preferred method, however other methods of positioning are available to the user. For example, the user could hold a switch in the hand not being used to hold the positioning device to avoid any movement of the transducer when the switch is depressed.

The standoff guide 7 is used to provide a proper contact between the ultrasonic transducer and the animal or carcass. The standoff guide is flexible to allow unbroken contact with the animal or carcass. This standoff guide is generally made of a polyvinyl chloride with a resin additive. Superflab™ and Flexgel™ are both types of PVC resin used for this purpose.

The trigger switch 12 allow the operator to signal a computer to "grab" a frame from the output of the ultrasound equipment. For use in a packing plant, generally all that is needed is a simple switch, however, for other applications, other controls could be included. For example, if video equipment is used in conjunction with the ultrasound equipment, the controls for the video equipment could be included. In fact, the six-pin connector 10 has two pins free for just this kind of expansion. While the signaling device is shown as "hard-wired", the signaling between the user and the computer, ultrasound equipment could be other means of communication, i.e. IR, sound, RF, etc.

Figure 5:
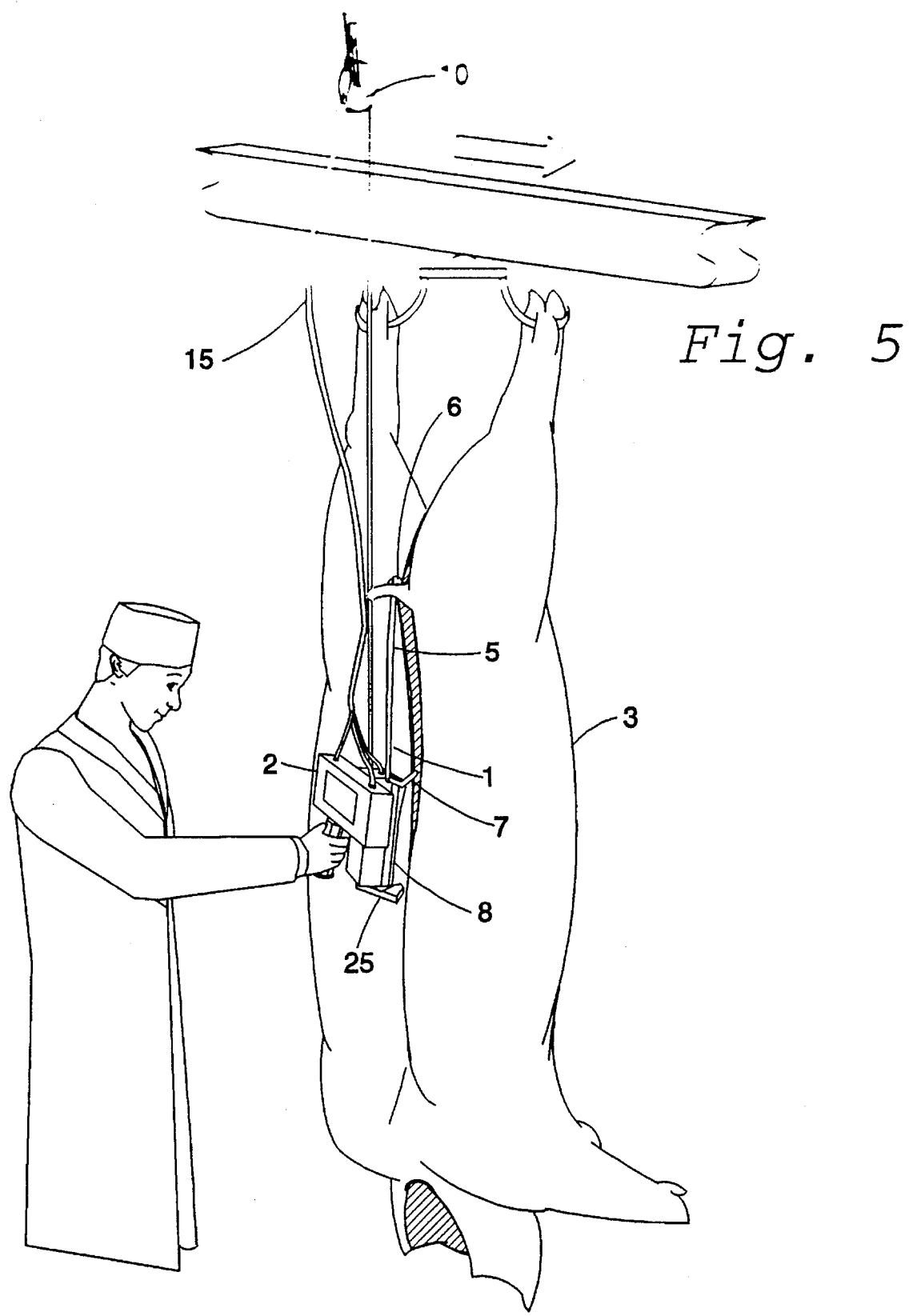
FIG. 5 shows a perspective view of an inspection of a meat carcass with one embodiment of the positioning apparatus taught by the present invention.

FIG. 5 shows the present invention being used in a packing plant to evaluate an animal carcass. As shown, the user only needs one hand to position the transducer 1. A counter balance 18 is connected to the counter balance hook 8. The positioning device can be used on a variety of animals or carcasses. When evaluating any livestock it is always more dangerous for the user to have to look away from the animal to see the image on a display screen. By using the present invention the user can watch the animal at all times while taking ultrasonic scans.

The positioning apparatus can include means for providing couplant fluid to the substrate to be ultrasonically scanned. As shown in FIG. 5, the positioning apparatus also includes a water sprayer for wetting the carcass. Water acts as an excellent couplant fluid on carcasses. However, for live animals an oil or jelly is usually preferable. Means for pumping and/or spraying these fluids or jellies are well known in the art, however, the use of the such devices in conjunction with an ultrasonic transducer positioning device is novel.

Figure 6:
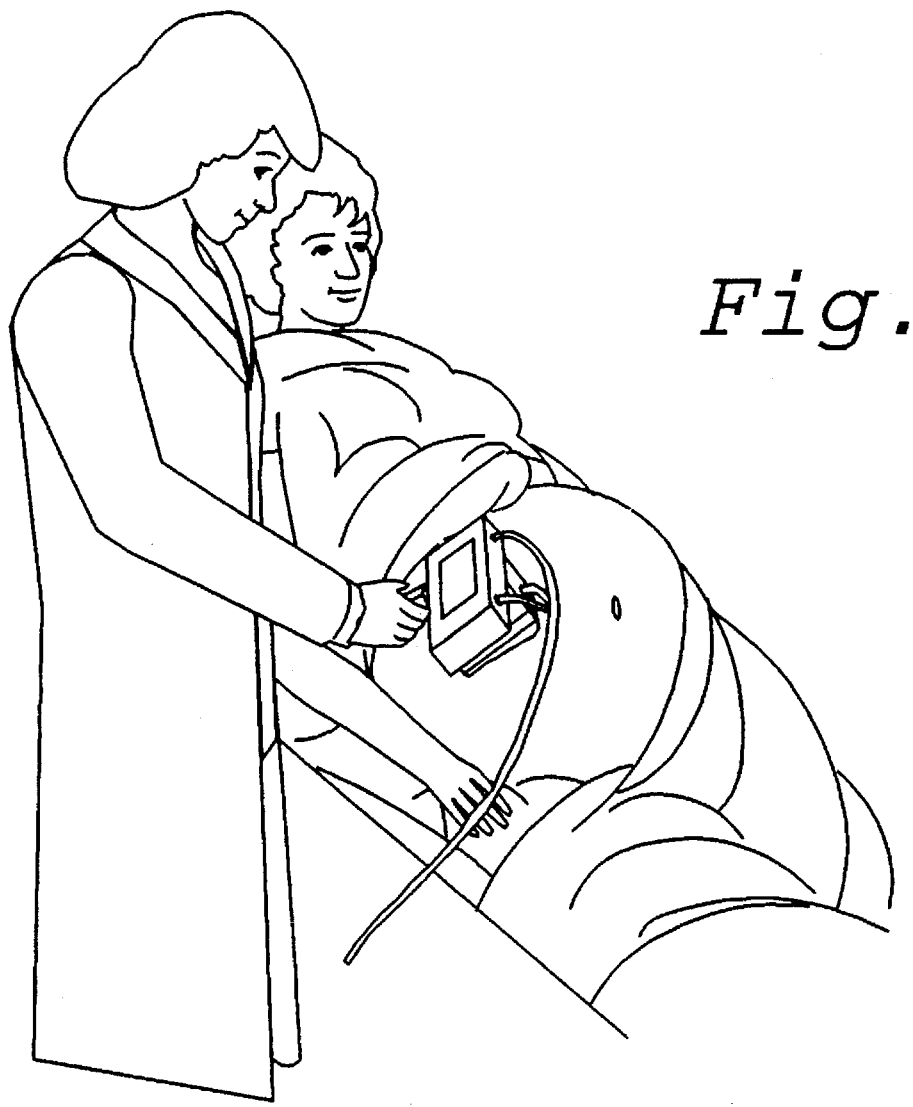
FIG. 6 shows a perspective view of a physician working with a patient with another embodiment of the positioning apparatus taught by the present invention.

FIG. 6 shows another embodiment of the present invention where a physician is using a transducer 1 and display positioning device of the present invention with a patient. This embodiment allows the physician to continue to look at the patient rather than have to continually look away at a monitor.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

What is claimed is:

1. An ultrasonic transducer and display screen positioning apparatus, operatively connected to ultrasonic equipment capable of capturing a real time ultrasonic image of an animal or carcass comprising:
   a) a handle;
   b) a transducer housing connected to said handle for securing said ultrasonic transducer;
   c) a display screen housing integral with said handle for securing said display screen connected to said transducer housing such that said display screen can display an image produced by ultrasonic scanning with said ultrasonic transducer in real time;
   d) a signaling device operatively associated with said ultrasound equipment; and,
   e) a ultrasonic transducer capable of providing electrical data to said ultrasound equipment such that an image of said animal or carcass being ultrasonically scanned is displayed on said display when the ultrasonic transducer is actuated.

2. The positioning apparatus of claim 1 further comprising means for attaching a counter balance.

3. The positioning apparatus of claim 1 further comprising means for indicating a uniform position for said ultrasonic transducer upon each animal or carcass, such that each animal or carcass may be evaluated with said positioning device.

4. The positioning apparatus of claim 1 wherein said ultrasonic transducer and said display screen are enclosed within a water tight housing.

5. The positioning apparatus of claim 4 wherein said ultrasonic transducer and said display screen are operatively associated with sealed electrical connectors.

6. The positioning apparatus of claim 1 further comprising means for securing a standoff guide to said transducer.

7. The positioning apparatus of claim 1 further comprising means connected to said handle for providing coupliant fluid on a substrate to be ultrasonically scanned.

8. The method of using a positioning apparatus of claim 1 to position said ultrasonic transducer.

9. A method for capturing an ultrasonic image of an animal or carcass using, an ultrasonic transducer and display screen, operatively connected to ultrasonic equipment capable of capturing said image, comprising the steps of:
   a) providing a handle with a transducer housing;
   b) securing an ultrasonic transducer within said housing;
   c) selecting a desired position for said ultrasonic transducer;
   d) providing said display screen such that said display screen can display an image produced by ultrasonic scanning with said ultrasonic transducer and said display screen and said ultrasonic transducer can both be seen clearly by the operator of said ultrasonic scanner when said transducer is placed into said uniform position;
   e) placing said ultrasonic transducer into said uniform position;
   f) providing a signaling device operatively associated with said ultrasound equipment;
   g) using said ultrasonic transducer to provide electrical data and a real time ultrasonic image of an animal or carcass such that an image of said animal or carcass being ultrasonically scanned is displayed on said display when the ultrasonic transducer is actuated; and,
   h) activating said signaling device whereby the image displayed on said display screen is captured.

10. The method of claim 9 further comprising the steps of:

a) viewing said image shown in said display screen after said ultrasonic transducer is placed into said uniform position; and b) making any necessary adjustments to achieve a desired image so as to provide for real time video capture as well as storage of image information on computer equipment for later analysis or recall of said image.

11. The method of claim 9 further comprising the step of providing means for indicating a uniform position for said ultrasonic transducer upon each animal or carcass, evaluated with said positioning device.

12. The method of claim 9 further comprising the step of enclosing said ultrasonic transducer and said display screen within a water tight housing.

13. The method of claim 9 further comprising the step of providing means for securing a standoff guide to said transducer.

14. The method of claim 9 further comprising the step of providing means for providing coupliant fluid on a substrate to be ultrasonically scanned.

15. The method of claim 9 wherein said desired position is on an animal or carcass.

16. The method of claim 9 wherein said desired position is on a human.

* * * * *